(12) United States Patent
Robertson et al.

(10) Patent No.: US 8,540,664 B2
(45) Date of Patent: Sep. 24, 2013

(54) PROBABLISTIC PHARMACOKINETIC AND PHARMACODYNAMIC MODELING

(75) Inventors: Timothy Robertson, Belmont, CA (US); Yashar Behzadi, San Francisco, CA (US)

(73) Assignee: Proteus Digital Health, Inc., Redwood Ctiy, CA (US)

( * ) Notice: Subject to any disclaimer, the term of this patent is extended or adjusted under 35 U.S.C. 154(b) by 0 days.

(21) Appl. No.: 13/260,073

(22) PCT Filed: Mar. 24, 2010

(86) PCT No.: PCT/US2010/028518
§ 371 (c)(1), (2), (4) Date: Sep. 23, 2011

(87) PCT Pub. No.: WO2010/111403
PCT Pub. Date: Sep. 30, 2010

(65) Prior Publication Data
US 2012/0022443 A1    Jan. 26, 2012

Related U.S. Application Data

(60) Provisional application No. 61/163,359, filed on Mar. 25, 2009.

(51) Int. Cl.
*A61M 5/168* (2006.01)
*G08B 1/08* (2006.01)

(52) U.S. Cl.
USPC ......... 604/65; 604/66; 340/10.1; 340/539.12; 340/572.1; 600/302

(58) Field of Classification Search
USPC ............ 604/65–66; 600/301–302; 340/10.1, 340/539.12, 572.1
See application file for complete search history.

(56) References Cited

U.S. PATENT DOCUMENTS

| | | | |
|---|---|---|---|
| 3,589,943 A | 6/1971 | Grubb et al. | |
| 3,607,788 A | 9/1971 | Adolph | |

(Continued)

FOREIGN PATENT DOCUMENTS

| | | |
|---|---|---|
| EP | 0344939 | 12/1989 |
| EP | 1246356 | 10/2002 |

(Continued)

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.

(Continued)

*Primary Examiner* — Quynh-Nhu H Vu
(74) *Attorney, Agent, or Firm* — Bozicevic, Field & Francis LLP; Bret E. Field

(57) ABSTRACT

The subject matter disclosed herein provides a response to a dose of a substance and/or controls the administration of the dose. In one aspect, there is provided a system. The system may include a processor and at least one memory configured to provide a response determinator. The response determinator may receive therapeutic and wellness data. Moreover, the response determinator may determine a response based on the received therapeutic and wellness data. The response may represent a reaction to a substance integrated with an ingestible event marker. The determined response may be provided to, for example, a therapy controller. Related systems, methods, and articles of manufacture are also described.

13 Claims, 9 Drawing Sheets

(56) References Cited

U.S. PATENT DOCUMENTS

| | | |
|---|---|---|
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,799,802 A | 3/1974 | Schneble, Jr. et al. |
| 3,828,766 A | 8/1974 | Krasnow |
| 3,837,339 A | 9/1974 | Aisenberg et al. |
| 3,893,111 A | 7/1975 | Cotter |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,494,950 A | 1/1985 | Fischell |
| 4,559,950 A | 12/1985 | Vaughan |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,725,997 A | 2/1988 | Urquhart et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,844,076 A | 7/1989 | Lesho |
| 4,896,261 A | 1/1990 | Nolan |
| 4,975,230 A | 12/1990 | Pinkhasov |
| 4,987,897 A | 1/1991 | Funke |
| 5,016,634 A | 5/1991 | Vock et al. |
| 5,079,006 A | 1/1992 | Urquhart |
| 5,167,626 A | 12/1992 | Casper |
| 5,176,626 A | 1/1993 | Soehendra |
| 5,261,402 A | 11/1993 | DiSabito |
| 5,263,481 A | 11/1993 | Axelgaard et al. |
| 5,279,607 A | 1/1994 | Schentag et al. |
| 5,281,287 A | 1/1994 | Lloyd |
| 5,283,136 A | 2/1994 | Peled et al. |
| 5,305,745 A | 4/1994 | Zacouto |
| 5,318,557 A * | 6/1994 | Gross .................. 604/891.1 |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,485,841 A | 1/1996 | Watkin et al. |
| 5,567,210 A | 10/1996 | Bates et al. |
| 5,596,302 A | 1/1997 | Mastrocola et al. |
| 5,600,548 A | 2/1997 | Nguyen et al. |
| 5,634,468 A | 6/1997 | Platt |
| 5,645,063 A | 7/1997 | Straka et al. |
| 5,705,189 A | 1/1998 | Lehmann et al. |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,845,265 A | 12/1998 | Woolston |
| 5,862,803 A | 1/1999 | Besson |
| 5,868,136 A | 2/1999 | Fox |
| 5,925,030 A | 7/1999 | Gross et al. |
| 5,957,854 A | 9/1999 | Besson et al. |
| 5,963,132 A | 10/1999 | Yoakum et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,091,975 A | 7/2000 | Daddona et al. |
| 6,095,985 A | 8/2000 | Raymond et al. |
| 6,115,636 A | 9/2000 | Ryan |
| 6,122,351 A | 9/2000 | Schlueter, Jr. et al. |
| 6,141,592 A | 10/2000 | Pauly |
| 6,200,265 B1 | 3/2001 | Walsh et al. |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,342,774 B1 | 1/2002 | Kreisinger et al. |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,394,997 B1 | 5/2002 | Lemelson |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,496,705 B1 | 12/2002 | Ng et al. |
| 6,526,315 B1 | 2/2003 | Inagawa |
| 6,531,026 B1 | 3/2003 | Takeichi et al. |
| 6,544,174 B2 | 4/2003 | West |
| 6,564,079 B1 | 5/2003 | Cory |
| 6,572,636 B1 | 6/2003 | Hagen et al. |
| 6,577,893 B1 | 6/2003 | Besson et al. |
| 6,579,231 B1 | 6/2003 | Phipps |
| 6,595,929 B2 | 7/2003 | Stivoric |
| 6,605,038 B1 | 8/2003 | Teller |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,800,060 B2 | 10/2004 | Marshall |
| 6,801,137 B2 | 10/2004 | Eggers et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |

| Patent | Date | Inventor |
|---|---|---|
| 6,879,810 B2 | 4/2005 | Bouet |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,957,107 B2 | 10/2005 | Rogers et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,575,005 B2 | 8/2009 | Mumford |
| 7,616,111 B2 | 11/2009 | Covannon |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,756,587 B2 | 7/2010 | Penner et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 2001/0027331 A1 | 10/2001 | Thompson |
| 2001/0044588 A1 | 11/2001 | Mault |
| 2001/0051766 A1 | 12/2001 | Gazdzinski |
| 2002/0002326 A1 | 1/2002 | Causey et al. |
| 2002/0026111 A1 | 2/2002 | Ackerman |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |

| | | |
|---|---|---|
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115517 A1 | 6/2004 | Fukuda et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0090753 A1 | 4/2005 | Goor et al. |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0148883 A1 | 7/2005 | Boesen |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |

| | | |
|---|---|---|
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowski |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1* | 11/2008 | Zdeblick et al. ........... 340/572.1 |
| 2008/0288027 A1 | 11/2008 | Kroll |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076343 A1 | 3/2009 | James |
| 2009/0082645 A1 | 3/2009 | Hafezi et al. |
| 2009/0087483 A1 | 4/2009 | Sison |
| 2009/0088618 A1 | 4/2009 | Ameson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |

| Publication No. | Date | Inventor |
|---|---|---|
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0010330 A1 | 1/2010 | Rankers |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081894 A1 | 4/2010 | Zdeblick et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0168659 A1 | 7/2010 | Say et al. |
| 2010/0179398 A1 | 7/2010 | Say et al. |
| 2010/0185055 A1 | 7/2010 | Robertson |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0234706 A1 | 9/2010 | Gilland |
| 2010/0234715 A1 | 9/2010 | Shin |
| 2010/0234914 A1 | 9/2010 | Shen |
| 2010/0239616 A1 | 9/2010 | Hafezi et al. |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1 | 11/2010 | Hafezi et al. |
| 2010/0298730 A1 | 11/2010 | Tarassenko et al. |
| 2010/0312188 A1 | 12/2010 | Robertson et al. |
| 2010/0312580 A1 | 12/2010 | Tarassenko et al. |
| 2011/0009715 A1 | 1/2011 | O'Reilly et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0105864 A1 | 5/2011 | Robertson et al. |
| 2011/0124983 A1 | 5/2011 | Kroll et al. |
| 2011/0224912 A1 | 9/2011 | Bhavaraju et al. |
| 2011/0230732 A1 | 9/2011 | Edman et al. |
| 2012/0062371 A1 | 3/2012 | Radivojevic et al. |

FOREIGN PATENT DOCUMENTS

| | | |
|---|---|---|
| EP | 1534054 | 5/2005 |
| EP | 1702553 | 9/2006 |
| EP | 1789128 | 5/2007 |
| EP | 2143369 | 1/2010 |
| JP | 61072712 | 4/1986 |
| JP | 05-228128 | 9/1993 |
| JP | 2000-506410 | 5/2000 |
| JP | 2002263185 | 9/2002 |
| JP | 2005-073886 | 3/2005 |
| JP | 2005-087552 | 4/2005 |
| JP | 2005-304880 | 4/2005 |
| JP | 2006006377 | 1/2006 |
| JP | 2006509574 | 3/2006 |
| JP | 2007-313340 | 12/2007 |
| KR | 20060077523 | 7/2006 |
| WO | WO8802237 | 4/1988 |
| WO | WO9221307 | 12/1992 |
| WO | WO9308734 | 5/1993 |
| WO | WO9319667 | 10/1993 |
| WO | WO9739963 | 10/1997 |
| WO | WO9843537 | 10/1998 |
| WO | WO9959465 | 11/1999 |
| WO | WO0033246 | 6/2000 |
| WO | WO0147466 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO03050643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004066833 | 8/2004 |
| WO | WO2004066834 | 8/2004 |
| WO | WO2004066903 | 8/2004 |
| WO | WO2004068881 | 8/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005047837 | 5/2005 |
| WO | WO2005051166 | 6/2005 |
| WO | WO2005110238 | 11/2005 |
| WO | WO2006021932 | 3/2006 |
| WO | WO2006027586 | 3/2006 |
| WO | WO2006055892 | 5/2006 |
| WO | WO2006055956 | 5/2006 |
| WO | WO2006075016 | 7/2006 |
| WO | WO2006100620 | 9/2006 |
| WO | WO2006116718 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2006104843 | 1/2008 |
| WO | WO2008008281 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |

| | | |
|---|---|---|
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO09001108 | 12/2008 |
| WO | WO2008150633 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010080765 | 7/2010 |
| WO | WO2010080843 | 7/2010 |
| WO | WO2010107563 | 9/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |

OTHER PUBLICATIONS

Arshak et al., A Review and Adaptation of Methods of Object Tracking to Telemetry Capsules IC-Med (2007) vol. 1, No. 1, Issue 1, pp. 35 of 46.

"ASGE Technology Status Evaluation Report: wireless capsule endoscopy" American Soc. For Gastrointestinal Endoscopy (2006) vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; (2003); abstract.

Barrie, Heidelberg pH capsule gastric analysis. Texbook of Natural Medicine, (1992), Pizzorno, Murray & Barrie.

Bohidar et al., "Dielectric Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) p. 91-96.

Delvaux et al., "Capsule endoscopy: Technique and indications" Clinical Gastoenterology (2008) vol. 22, Issue 5, pp. 813-837.

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.

Ferguson et al., "Dialectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Gilson, D.R. "Molecular dynamics simulation of dipole interactions", Department of Physics, Hull University, Dec. 2002, p. 1-43.

Given Imaging, "Agile Patency Brochure" (2006) http://www.inclino.no/documents/AgilePatencyBrochure_Global_GMB-0118-01.pdf; 4pp.

Gonzalez-Guillaumin et al., "Ingestible capsule for impedance and pH monitoring in the esophagus" IEEE Trans Biomed Eng. (2007) 54(12): 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Heydari et al., "Analysis of the PLL jitter due to power/ground and substrate noise"; IEEE Transactions on Circuits and Systems (2004) 51(12): 2404-16.

ISFET—Ion Sensitive Field-Effect Transistor; MICROSENS S.A. pdf document. First in Office Action dated Jun. 13, 2011 for U.S. Appl. No. 12/238,345; 4pp.

INTROMEDIC, MicroCam Innovative Capsule Endoscope Pamphlet. (2006) 8 pp (http://www.intromedic.com/en/product/productinfo.asp).

Juvenile Diabetes Research Foundation International (JDRF), "Artificial Pancreas Project" (2010); http://www.artificialpancreasproject.com/; 3 pp.

Kamada K., "Electrophoretic deposition assisted by soluble anode" Materials Letters 57 (2003) 2348-2351.

Li, P-Y, et al. "An electrochemical intraocular drug delivery device", Sensors and Actuators A 143 (2008) p. 41-48.

LIFESCAN, "OneTouch UltraLink™" http://www.lifescan.com/products/meters/ultralink (2010) 2 pp.

MacKay et al., "Radio Telemetering from within the Body Inside Information is Revealed by Tiny Transmitters that can be Swallowed or Implanted in Man or Animal" Science (1991) 1196-1202; 134; American Association for the Advancement of Science, Washington D.C.

MacKay et al., "Endoradiosonde" Nature, (1957) 1239-1240, 179 Nature Publishing Group.

McKenzie et al., "Validation of a new telemetric core temperature monitor" J. Therm. Biol. (2004) 29(7-8):605-11.

MedTronic, "CareLink Therapy Management Software for Diabetes" (2010); https://carelink.minimed.com/patient/entry.jsp?bhcp=1; 1 pp.

MedTronic, "Carelink™ USB" (2008) http://www.medtronicdiabetes.com/pdf/carelink_usb_factsheet.pdf 2pp.

MedTronic "The New MiniMed Paradigm® Real-Time Revel™ System" (2010) http://www.medtronicdiabetes.com/products/index.html; 2 pp.

MedTronic, "Mini Med Paradigm® Revel™ Insulin Pump" (2010) http://www.medtronicdiabetes.com/products/insulinpumps/index.html; 2 pp.

MedTronic, Mini Med Paradigm™ Veo™ System: Factsheet (2010). http://www.medtronic-diabetes.com.au/downloads/Paradigm%20Veo%20Factsheet.pdf ; 4 pp.

Melanson, "Walkers swallow RFID pills for science" Engadget (2008); http://www.engadget.com/2008/07/29/walkers-swallow-rfid-pills-for-science/.

MiniMitter Co. Inc. "Actiheart" Traditional 510(k) Summary. Sep. 27, 2005.

MiniMitter Co. Inc. Noninvasive technology to help your studies succeed. MiniMitter.com Mar. 31, 2009.

Mini Mitter Co, Inc. 510(k) Premarket Notification Mini-Logger for Diagnostic Spirometer. Sep. 21, 1999.

Mini Mitter Co, Inc. 510(k) Premarket Notification for VitalSense. Apr. 22, 2004.

MiniMitter Co. Inc. VitalSense Integrated Physiological Monitoring System. Product Description. (2005).

MiniMitter Co. Inc. VitalSense Wireless Vital Signs Monitoring. Temperatures.com Mar. 31, 2009.

Mohaverian et al., "Estimation of gastric residence time of the Heidelberg capsule in humans: effect of varying food composition" Gastroenterology (1985) 89:(2): 392-7.

"New 'smart pill' to track adherence" E-Health-Insider (2010) http://www.e-health-insider.com/news/5910/new_'smart_pill'_monitors_medicines.

NPL_AntennaBasics.pdf, Radio Antennae, http://www.erikdeman.de/html/sail018h.htm; (2008) 3pp.

O'Brien et al., "The Production and Characterization of Chemically Reactive Porous Coatings of Zirconium Via Unbalanced Magnetron Sputtering" Surface and Coatings Technology (1996) 86-87; 200-206.

Park, "Medtronic to Buy MiniMed for $3.7 Billion" (2001) HomeCare; http://homecaremag.com/mag/medical_medtronic_buy_minimed/; 2 pp.

Philips Respironics (http//minimitter.com/products.cfm) Products, Noninvasive Technology to Help Your Studies Succeed. 510(k) Permanent Notification for Vital Sense. Apr. 22, 2004.

"RFID "pill" monitors marchers" RFID News (2008) http://www.rfidnews.org/2008/07/23/rfid-pill-monitors-marchers/.

Roulstone, et al., "Studies on Polymer Latex Films: I. A study of latex film morphology" Polymer International 24 (1991) pp. 87-94.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Santini, J.T. et al, "Microchips as controlled drug delivery-devices", Agnew. Chem. Int. Ed. (2000), vol. 39, p. 2396-2407.

"SensiVida minimally invasive clinical systems" Investor Presentation Oct. 2009 28pp; http://www.sensividamedtech.com/SensiVidaGeneralOctober09.pdf.

Shawgo, R.S. et al. "BioMEMS from drug delivery", Current Opinion in Solid State and Material Science 6 (2002), p. 329-334.

Shin et al., "A Simple Route to Metal Nanodots and Nanoporous Metal Films"; Nano Letters, vol. 2, No. 9 (2002) pp. 933-936.

Shrivas et al., "A New Platform for Bioelectronics—Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010.

"Smartlife awarded patent for knitted transducer" Innovation in Textiles News: http://www.innovationintextiles.com/articles/208.php; 2pp. (2009).

"The SmartPill Wireless Motility Capsule" SmartPill, The Measure of GI Health; (2010) http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Soper, S.A. et al. "Bio-Mems Technologies and Applications", Chapter 12, "MEMS for Drug Delivery", p. 325-346 (2007).

Swedberg, "University Team Sees Ingestible RFID Tag as a Boon to Clinical Trials" RFID Journal Apr. 27, 2010; http://www.rfidjournal.com/article/view/7560/1.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Tatbul et al., "Confidence-based data management for personal area sensor networks" ACM International Conference Proceeding Series (2004) 72.

Tierney, M.J. et al "Electroreleasing Composite Membranes for Delivery of Insulin and other Biomacromolecules", J. Electrochem. Soc., vol. 137, No. 6, Jun. 1990, p. 2005-2006.

University of Florida News "Rx for health: Engineers design pill that signals it has been swallowed" (2010) 2pp.; http://news.ufl.edu/2010/03/31/antenna-pill-2/.

U.S. Appl. No. 12/238,345, filed Sep. 25, 2008, Hooman et al., Non-Final Office Action mailed Jun. 13, 2011 22pp.

Walkey, "MOSFET Structure and Processing"; 97.398 Physical Electronics Lecture 20; First in Office Action dated Jun. 13, 2011 for U.S. Appl. No. 12/238,345; 24 pp.

Watson, et al., "Determination of the relationship between the pH and conductivity of gastric juice" Physiol Meas. 17 (1996) pp. 21-27.

Wongmanerod et al., "Determination of pore size distribution and surface area of thin porous silicon layers by spectroscopic ellipsometry" Applied Surface Science 172 (2001) 117-125.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3, 2006.

Zimmerman, "Personal Area Networks: Near-field intrabody communication" IBM Systems Journal (1996) 35 (3-4):609-17.

Description of ePatch Technology Platform for ECG and EMG, located it http://www.madebydelta.com/imported/images/DELTA_Web/documents/ME/ePatch_ECG_EMG.pdf, Dated Sep. 2, 2010.

Zworkin, "A Radio Pill" Nature, (1957) 898, 179 Nature Publishing Group.

Gaglani S. "Put Your Phone, or Skin, on Vibrate" MedGadget (2012) http://medgadget.com/2012/03/put-your-phone-or-skin-on-vibrate.html 8pp.

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Rolison et al., "Electrically conductive oxide aerogels: new materials in electrochemistry" J. Mater. Chem. (2001) 1, 963-980.

Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

* cited by examiner

PROBABLISTIC PHARMACOKINETIC AND PHARMACODYNAMIC MODELING

CROSS-REFERENCE TO RELATED APPLICATIONS

This application claims the benefit of U.S. Provisional Patent Application No. 61/163,359, filed Mar. 25, 2009 and titled "Probabilistic Pharmacokinetic and Pharmacodynamic Modeling", incorporated by reference for all purposes in the Present Application.

INTRODUCTION

Pharmacokinetics (PK) refers to determining the effects of a substance, such as a drug, a nutrient, a metabolite, a hormone, a toxin, and any other compound, administered to an organism, such as a human. For example, pharmacokinetics includes analyzing the mechanisms of absorption and distribution of an administered drug, the rate at which a drug action begins, the duration of the effect, chemical changes of the substance in the organism (e.g., by enzymes), and the effects and routes of excretion of the metabolites of the drug. Unlike pharmacokinetics, pharmacodynamics (PD) refers to determining what the substance does to the organism. For example, pharmacodynamics includes analyzing drug actions on the organism, such as whether the drug depresses, stimulates, destroys, irritates, or replaces substances within the organism. Pharmacokinetics and/or pharmacodynamics may be used to determine the administration of the substance to the organism.

SUMMARY

The subject matter disclosed herein provides a response and/or controls the administration of one or more doses.

In one aspect, there is provided a system. The system may include a processor and at least one memory configured to provide a response determinator. The response determinator may receive therapeutic and wellness data. Moreover, the response determinator may determine a response based on the received therapeutic and wellness data. The response may represent a reaction to a substance integrated with an ingestible event marker. The determined response may be provided to, for example, a therapy controller.

In another aspect, there is provided a system. The system may include a processor and at least one memory configured to provide a therapy controller. The therapy controller may receive a response representing a reaction to a substance integrated with an ingestible event marker. Moreover, the therapy controller may receive therapeutic and wellness data. Furthermore, at least one of a dose of the substance and a time of the dose of the substance may be controlled based on the received response and the received therapeutic and wellness data.

In one aspect, there is provided a method. The method may include receiving therapeutic and wellness data including ingestible event marker data and determining a response based on the received therapeutic and wellness data. The response may represent a reaction to a substance integrated with an ingestible event marker. The determined response may be provided to, for example, a therapy controller.

In another aspect, there is provided a method. The method may include receiving a response representing a reaction to a substance integrated with an ingestible event marker; receiving therapeutic and wellness data; and controlling, based on the received response and the received therapeutic and wellness data, at least one of a dose of the substance and a time of the dose of the substance.

In one aspect, there is computer-readable medium. The computer-readable medium may include instructions to configure a processor to perform a method. The method may include receiving therapeutic and wellness data and determining a response based on the received therapeutic and wellness data. The response may represent a reaction to a substance integrated with an ingestible event marker. The determined response may be provided to, for example, a therapy controller.

In one aspect, there is computer-readable medium. The computer-readable medium may include instructions to configure a processor to perform a method. The method may include receiving a response representing a reaction to a substance integrated with an ingestible event marker; receiving therapeutic and wellness data; and controlling, based on the received response and the received therapeutic and wellness data, at least one of a dose of the substance and a time of the dose of the substance.

One or more of the above aspects may also include one or more of the following features. The therapeutic and wellness data may include ingestible event marker data received from the ingestible event marker integrated with the substance. The ingestible event marker may provide a signal when the substance is ingested. The therapeutic and wellness data may include data representative of physiological aspects associated with the ingestion of the ingestible event marker and the substance. The therapeutic and wellness data may include one or more of the following: an ingestion time; an identification of the substance; an expiration date of the substance; a dosage amount for the substance; one or more physiological parameters associated with the reaction to at least one dose of the substance; a dosage of an intravenous substance; a heart rate; a blood pressure measurement; an optical measurement; a body temperature; a weight; an amount of an inhalant; an inhalation time; an identity of an inhaled substance; a galvanic skin response; an insertion time; and a drinking time. The response determinator may further determine the response as a function of the therapeutic and wellness data. The response determinator may determine the response as a response matrix, H, according to the following equation:

$$H(A^T A)^{-1} A^T Y,$$

wherein A represents one or more times that a dose of the substance is ingested, $A^T$ represents a transpose of matrix A, $(A^T A)^{-1}$ represents an inverse of a matrix multiplication of matrix A and matrix $A^T$, and Y represents a matrix of observations comprising the therapeutic and wellness data.

Moreover, a therapy controller may be configured to control, based on the response, at least one of an amount the substance and a time of the substance is ingested. The therapy controller may include a closed-loop to control at least one of the dose of the substance and the time of the dose of the substance. The therapy controller may use a closed-loop to vary an input to the response to generate an output of the response, and the output may correspond to at least one of the dose of the substance and the time of the dose of the substance. The response may be determined based on the reaction of at least one of an individual patient, a population, and a subset of the population.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

Such incorporations include United States Patent Application Publication No. 20080284599 published on Nov. 20, 2008 titled "Pharma-Informatics System"; United States Patent Application Publication No. 20090135886 titled "Transbody Communication Systems Employing Communication Channels", United States Patent Application No. 20090082645, published on Mar. 26, 2009 titled "In-Body Device With Virtual Dipole Signal Amplification"; U.S. patent application Ser. No. 12/546,017 filed Sep. 21, 2009 titled, "Communication System With Partial Power Source"; PCT Patent Application No. U.S. Ser. No. 09/68128 filed Dec. 15, 2009 titled "Body-Associated Receiver and Method"; and U.S. patent application Ser. No. 12/398,941, filed Mar. 5, 2009 titled Multi-Mode Communication Ingestible Event Marker System, and Methods of Using the Same.

Such incorporations further include Patent Applications filed under the Patent Cooperation Treaty ("PCT"), to include PCT Patent Application Serial No. PCT/US2006/016,370, filed Apr. 28, 2006; PCT Patent Application Serial No. PCT/US07/82563, filed Oct. 17, 2007; PCT Patent Application Serial No. PCT/US2008/52845 filed Feb. 1, 2008; PCT Patent Application Serial No. PCT/US2006/016370 published as WO/2006/116718; PCT Patent Application Serial No. PCT/US2007/082563 published as WO/2008/052136; PCT Patent Application Serial No. PCT/US2007/024225 published as WO/2008/063626; PCT Patent Application Serial No. PCT/US2007/022257 published as WO/2008/066617.

The publications discussed or mentioned herein are provided solely for their disclosure prior to the filing date of the present application. Nothing herein is to be construed as an admission that the present invention is not entitled to antedate such publication by virtue of prior invention. Furthermore, the dates of publication provided herein may differ from the actual publication dates which may need to be independently confirmed.

BRIEF DESCRIPTION OF THE DRAWINGS

In the drawings.

Like labels will be used to refer to the same or similar elements.

DETAILED DESCRIPTION

The subject matter described herein may provide a system including a response determinator configured to provide a response representative of at least one of an amount of a dose (e.g., an amount) of a substance and a time the dose should be administered. Moreover, a therapy controller may also be provided. The therapy controller may use a response, such as the response determined by the response determinator, to control the administration of the substance. Before the response determinator and therapy controller are described in detail with respect to FIGS. 2-8, FIG. 1 provides an example framework in which the response determinator and therapy controller may be used.

Figure 1:
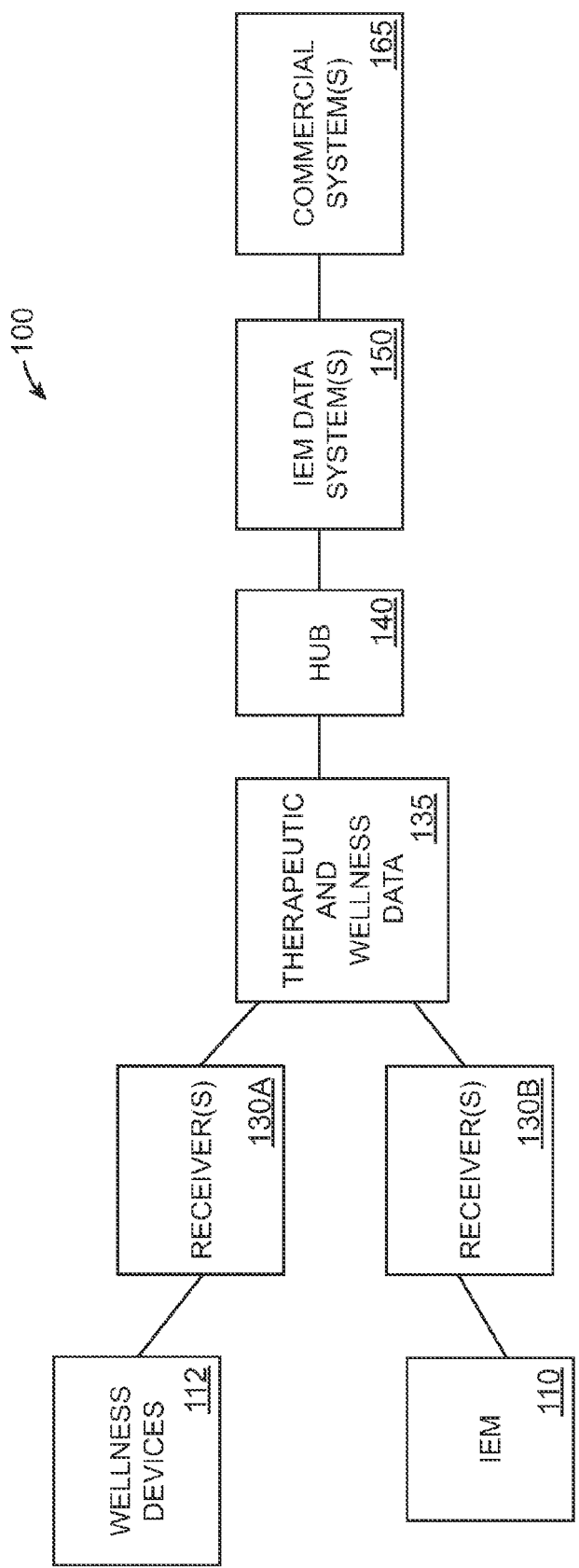
FIG. 1 depicts a system including an ingestible event marker (IEM)

FIG. 1 depicts a system 100 including an ingestible event marker (IEM) 110, wellness devices 112, one or more receivers 130A-B, therapeutic and wellness data 135, a hub 140, one or more IEM data systems 150, and one or more commercial systems 165. The therapeutic and wellness data 135 may include IEM data from the IEM 110 and/or other data from the wellness devices 112. For example, therapeutic and wellness data 135 may include IEM data representative of events, such as drug ingestion, intravenous medication delivery, and the like. The wellness data may include physiologic data, such as heart rate, activity, and other metrics, described below.

The IEM 110 refers to a device that may be, for example, ingested, and may be integrated with a substance, such as a drug, a nutrient, a metabolite, a hormone, a toxin, and any other compound. The IEM 110 may mark the ingestion as an event. The IEM 110 may include an identifier activated upon contact with a target site, such as the internal digestive tract of an organism. Once activated, the identifier of the IEM 110 provides (e.g., generates, emits, transmits, etc.) a signal, which may be detected by the receiver 130B described further below.

Although the above describes the target site as the digestive tract, the target site may be any location that activates the IEM 110 or the identifier of the IEM 110. For example, the target site may include physiological sites, a location in the gastrointestinal tract, such as the mouth, esophagus, stomach, small intestine, large intestine, and the like. Moreover, the identifier of IEM 110 is configured to be activated upon contact with fluid in the target site. The IEM 110 may also mark other events associated with a therapy, such as an inhalation event, an injection event, an implantation, an insertion event, and the like For example, the IEM 110 may be integrated into an intravenous (IV) bag, a syringe, an inhaler, and/or other devices to mark therapeutic events associated with those devices.

The signal emitted by the identifier of IEM 110 may be a generic signal, such as a signal that merely identifies that the IEM 110 has contacted the target site, or a unique signal, such as a signal uniquely identifying a particular IEM 110 from a plurality of other IEMs. For example, the signal may be unique in the sense that the signal is unique to a dose, e.g., each dose has an identifier signal that is unique when compared to other doses, or to a batch, e.g., the doses within a batch have the same identifier signal but that signal is different from other signals from other batches. The signal from the IEM 110 may either directly convey information about a given event, or provide an identifying code, which may be used to retrieve information about the event from a database linking the identifying code with a composition bound to the IEM 110.

The identifier of IEM 110 may generate a variety of signals including radio frequency (RF) signals, magnetic signals, conductive (near field) signals, acoustic signals, etc. The transmission time of the identifier sent by the IEM 110 may vary from about 0.1 microseconds to about 48 hours or longer. The identifier of IEM 110 may be transmitted once or repeatedly transmitted to provide redundancy, enhancing the ability of receiver 130 to detect the identifier of IEM 110. The identifier of IEM 110 may be dimensioned to be orally ingestible, e.g., either by itself or upon combination with a physiologically acceptable carrier component of the composition to produce a composition that can be readily administered to a subject in need of the composition. For example, the IEM 110 may be dimensioned to have a width ranging from about 0.05 millimeters to about 2 or more millimeters, although other sizes may be used as well. The identifier of IEM 110 may take a variety of different configurations, such as a chip configuration, a cylinder configuration, a spherical configuration, a disc configuration, and/or any other configuration suitable for its intended application, method of manufacture, etc.

The identifier of IEM 110 may be programmable, field programmable, mass programmable, fuse programmable, and/or reprogrammable. In some implementations, the signal generated by the identifier of IEM 110 may be determined after production, e.g., after initial production and following incorporation into a substance, such as a drug.

Although a variety of technologies may be used, in some implementations, radio frequency identification (RFID) smart tag technology may be used in the identifier of IEM 110. With RFID or other smart tag technology, a manufacturer or a vendor may associate a unique identifier code with a given identifier of IEM 110, even after the identifier has been incorporated into the composition, medication, and the like. Moreover, each individual or entity involved in the handling of the composition before use may introduce information into the identifier of IEM 110, which can be included in the signal emitted by the IEM 110.

The identifier of IEM 110 may include a memory element having variable capacity. For example, the memory element of IEM 110 may have a capacity ranging from about 1 bit to about 1 gigabyte or more.

In some implementations, the identifier of IEM 110 may include an activation component and a signal generation component. The activation component activates the signal generation component to provide a signal, e.g., by emission or upon interrogation, following contact of the IEM 110 with the target site, such as the stomach. The activation of the identifier of IEM 110 may be achieved in a number of different ways, including battery completion, battery connection, etc. In the case of battery completion, the activation component employs a battery that includes a cathode, an anode, and, when completed, an electrolyte. The electrolyte is made up, at least in part, by fluid present at the target site. For example, when the IEM 110 travels through the esophagus and enters the stomach, the stomach fluids activate an ingested IEM 110. In this example, the cathode and anode provided in the IEM 110 do not constitute a full battery. However, when the cathode and anode are exposed to stomach fluid, the stomach fluid acts as the electrolyte component of the battery and completes the battery. Therefore, as the IEM 110 contacts the target site, a power source is provided which activates the identifier of the IEM, and a signal is then transmitted.

In some implementations, the battery that is employed is one that comprises two dissimilar electrochemical materials comprising the anode and the cathode of the battery. When the electrode materials are exposed and come in contact with the target site, such as stomach acid or other types of fluid, a voltage may be generated between the electrodes as a result of the respective oxidation and reduction reactions that occur. The two dissimilar materials in an electrolyte are at different potentials. As an example, copper and zinc when put into a cell have different potentials. Similarly, gold and magnesium have different potentials.

The wellness devices 112 may include one or more of the following devices: a sensor, an intravenous delivery mechanism, a syringe, a pacemaker, a blood pressure sensor, a blood glucose monitor, an optical device for measuring blood serum, a temperature sensor, a heart rate monitor, an intelligent scale, intelligent blood pressure cuffs, an intelligent refrigerator monitoring usage of its contents, or any other mechanism configured to provide data usable in system 100. For example, in some implementations, a device, such as a mobile phone, computer, and the like, is configured with an application to allow a user to provide subjective measures of wellness, e.g., input into a browser a perceived wellness on a scale of 1-10.

Moreover, the wellness devices 112 may be "intelligent" devices, which refer to one or more devices capable of generating and/or communicating data via a communication link, such as a wired and/or a wireless link, to a destination. The wellness devices 112 may also be configured to provide the therapeutic and wellness data 135 to at least one of the receivers 130A-B using a wired and/or a wireless link. For example, a heart rate monitor may provide heart rate measurements wirelessly to a receiver 130A specifically configured to operate only with the heart rate monitor, or may provide the measurements to receiver 130B configured to accept the heart rate measurements and the signal from the IEM 110.

The wellness devices 112 may generate data, which may be included in, processed with, and/or correlated with IEM data provided by IEMs to form therapeutic and wellness data 135. This therapeutic and wellness data 135 is then forwarded to the hub 140, IEM data systems 150, and/or commercial systems 165. The wellness devices 112 may be attachable, implantable, semi-implantable, or otherwise associated with an organism, such as the human body.

The system 100 may include one or more receivers 130A-B. The receivers 130A-B may detect (e.g., receive, decode, and the like), and forward data received from a device, such as the IEM 110 or a wellness device 112. For example, the receiver 130B may receive a signal from the IEM 110, decode the signal into data, and forward the IEM data, as therapeutic and wellness data 135, to hub 140 and an IEM data system 150. The receivers 130A-B may receive, from IEM 110 and/ wellness devices 112, the signal carrying data via a wireless link, a wired link, or a combination of both.

The receivers 130A-B may be implemented in various ways, including an implantable device, a semi-implantable device, such as a subcutaneous device, and an externally applied device, such as a personal signal receiver. One example of a personal signal receiver is a "patch" receiver removably affixed to the skin or apparel of a user. In some implementations, receiver 130A may be implemented as a personal health signal receiver associated with the body, e.g., located inside or within close proximity to a body, configured to receive and decode a signal from an in vivo transmitter located inside the body.

Although FIG. 1 depicts receiver 130A and B as separate, in some implementations, the receivers 130A-B may be implemented as a single receiver configured to receive signals, or data carried by the signals, from IEM 110 and wellness devices 112, and then forward the data to hub 140, IEM data systems 150, and/or commercial systems 165.

In implementations where the receiver is affixed or otherwise associated with an individual user, programming logic associated with the receiver 130A-B may receive a signal carrying actual data samples of the individual, e.g., from data sources including heart devices, IEM 110, etc. The receiver 130A-B may communicate the actual data samples received from the data sources and the unique identifier(s) received from the IEM(s) to a processor, e.g., a computer at IEM data system 150. The processor may compare the actual data samples of the individual with the unique identifier to verify that the medication was actually ingested by the particular patient for whom it was prescribed. In various aspects, predetermined actions based on the verification outcome may be taken, e.g., alerts may be sent to a device associated with the commercial system 165, such as a prescription system used by a prescribing physician or a pharmacist.

In some implementations, the therapeutic and wellness data 135 may be generated, received, gathered, etc., from one or more sources including IEM 110 and/or wellness devices 112. Moreover, the therapeutic and wellness data 135 may comprise various structures, content, types, and the like, and may be provided by the IEM 110 and/or the wellness devices 112.

The therapeutic and wellness data 135 may include data associated with at least one of an ingestion event (which is signaled by an IEM 110 and received at a receiver 1308) and a response to the ingestion event. The ingestion event, which is signaled by IEM 110, may be associated with, for example, data related to and/or gathered during transit through the alimentary system, e.g., oral cavity, pharynx, esophagus, stomach, small intestine, large intestine, anus, etc. For example, the IEM 110 may provide IEM data in response to ingestion event, and the corresponding IEM data may include one or more of the following: an ingestion time, identification of ingested substance (also referred to as a composition, drug, medication, and the like), an expiration date of an associated medication, dosage of an ingested substance, etc.

The information about a response to the ingestion event may include, for example, physiologic parameter(s), such as a physiologic status or physiologic change event based on the ingestion event. A physiologic status may be, for example, a heart rate, a blood pressure measurement, and the like which are ascertained in close temporal proximity to the time of ingestion. Moreover, the information about a response to the ingestion event may be obtained from the IEM 110, wellness devices 112, and the corresponding receivers 130A-B.

Moreover, the generation of therapeutic and wellness data 135 via multiple IEMs 110 and wellness devices 112 may provide comprehensive data reporting, e.g., data generated from multiple ingestion events of multiple IEMs 110 over a time interval, data generated from multiple IEMs 110 ingested at approximately the same time, etc. In this manner, comprehensive therapeutic and wellness data 135 may be provided. In some implementations, this comprehensive data may provide enhanced therapy, when compared to approaches using single events or single sources of data.

In various aspects, the therapeutic and wellness data 135 may be communicated to, i.e., received by, a receiver, such as receiver 130B. Moreover, the therapeutic and wellness data 135 may include data not associated with an ingestion event or a response. For example, the therapeutic and wellness data 135 may one or more of the following: an amount or dosage of a substance delivered intravenously, a time associated with the delivery of a substance or dosage, a heart rate measurement, a blood pressure measurement, optical measurements of the blood, a body temperature, a weight, a heart rate, a physiologic parameter, and the like.

The therapeutic and wellness data 135 may include IEM data, which further includes a unique identifier, e.g., the unique identifier of an individual may be further associated with heart rate variability, breathing rate, and/or heart rate (ECG) patterns associated with the particular individual. For example, the unique identifier, e.g., an alphanumeric code and the like, may be implemented as a personal identifier assigned to an individual. Another example is a unique identifier reflective of an individual trait, such as a physiologic pattern or a medical condition. To illustrate, a patient may ingest an IEM 110 integrated with medication. The IEM 110 may communicate the therapeutic and wellness data 135 (including IEM data) to a receiver, such as the receiver 130B configured as a patch receiver. Moreover, the IEM data may include the above-described unique identifiers, which may be compared to data at the receiver 1308 to validate that the data came from the individual being monitored and/or to indicate the individual trait, such as a physiologic pattern or a medical condition. Although the above describes the IEM data originating from a device, such as IEM 110, that is ingested, the IEM data, as well as the therapeutic and wellness data 135, may be from one or more of the following: an inhalable device, an injectable device, an implantable device, an insertable device, and an imbibable device, and the therapeutic and wellness data 135.

The inhalable device may include, for example, a microchip attached to, embedded in, or otherwise integrated with a device. The inhalable device is capable of determining parameter(s) associated with inhalation, e.g., measuring or tallying doses of an inhalant, inhalation time, identify an inhaled substance, etc.

The injectable device may include, for example, a microchip attached to, embedded in, or otherwise integrated with a device. The injectable device is capable of ascertaining parameter(s) associated with injection, e.g., time of injection, identification of an injected substance, etc. The injectable device may be configured to be injected into a human body or a non-human body, e.g., injection into the circulatory system.

The implantable device may include, for example, a microchip attached to, embedded in, or otherwise integrated with a device. The implantable device is capable of ascertaining parameter(s) associated with implantation, e.g., time of implantation, physiologic parameters such as heart rate, EKG data, activity management data, temperature, galvanic skin response data, respiratory data, fluid status data, heart rate variability, etc. The implantable device may be implemented as an implantable receiver 130A for receiving various data. The implantable receiver may also process, store, transmit, etc. data to hub 140, as well as other devices. Various other implantable devices include, for example, heart monitors and the like having a microchip to ascertain parameter(s), e.g., heart rate, heart pressure, etc.

The insertable device may include, for example, a microchip. The microchip may be independently deployed inside the body, e.g., implemented as a microchip mechanically associated with a suppository for rectal insertion, vaginal insertion, etc. The microchip may also be attached to, embedded in, or otherwise integrated within another device. The insertable device is capable of ascertaining parameter(s) associated with insertion, e.g., time of insertion, physiologic parameters such environmental content/fluid identification, etc.

The imbibable device may include, for example, a microchip attached to, embedded in, or otherwise integrated with a substance, e.g., a potable solution or fluid such as a beverage, etc. The imbibable device is capable of ascertaining parameter(s) associated with imbibing, e.g., time of drinking, physiologic parameters such as environmental content/fluid identification, etc. The imbibable device may be implemented as a microchip and imbibed together with a beverage, which may aid in swallowing and used as a medication, etc.

Further, the therapeutic and wellness data 135 may be associated with administration of a therapeutic agent, etc. For example, administration includes, but is not limited to, parenteral administration, i.e., administration in a manner other than through the alimentary system.

The hub 140 may provide the therapeutic and wellness data 135 to another device, such as the IEM data system 150. For example, the hub 140 may receive the therapeutic and wellness data 135 from receiver 130B and IEM 110, and then forward the therapeutic and wellness data 135 to one or more of the IEM data systems 150. The hub 140 may be included within any other device. For example, the hub 140 may be implemented as one or more of the following: a personal communication device, a base station, a mobile telephone, and any other device configured to receive therapeutic and wellness data 135 and forward that data to another device.

The hub 140 may be configured to execute software, such as a software agent, or an application, to process therapeutic and wellness data 135. For example, a software agent may be preconfigured, e.g., configurable by the manufacturer, retailer, or consumer, and configurable after download from, for example, a storage medium or a website. In one implementation, the downloaded software is an auto-refill application related to or integrated with a commercial system 165, e.g., an auto-refill system to facilitate automated prescription refill functions. In some implementations, the hub 140 may be incorporated into one or more of the IEM 110, wellness devices 112, receivers 130A-B, IEM data system 150, and the like.

For example, the hub 140 may be implemented using a personal communication device including communication and processing functionality. Examples of personal communication devices include a handheld device or a computer configured with a communication capability, such as WiFi, Bluetooth, GSM, and/or any other wireless mechanism. The personal communication device may include a processor, a display screen with a touch input functionality, a miniature keyboard, etc. Examples of handheld devices include a personal digital assistant (PDA), smart phones, enterprise digital assistants offering integrated data capture devices like bar code, radio frequency identification (RFID), and smart card readers, etc.

The base station may be implemented as any device or appliance capable of receiving data, such as the therapeutic and wellness data 135. Examples of base stations include computers, such as desktop computers and laptop computers, and intelligent devices/appliances. The base station includes systems, subsystems, devices, and/or components that receive, transmit, and/or relay the therapeutic and wellness data 135. In various aspects, the base station communicably interoperates with a receiver and a communications network, such as the Internet. In various aspects, the base station may be embodied as an integrated unit or as distributed components, e.g., a desktop computer and a mobile telephone in communication with one another and in communication with a receiver and the Internet and/or a wireless network.

Furthermore, the base station may be incorporated into and/or communicate with various devices. These various devices include, for example, clock radios; intelligent pill dispensers; pill managers, e.g., devices capable of receiving various substances and producing a combined substance, dose(s) of substances, etc.; pharmaceutical compounding devices; intelligent devices such as scales; blood pressure measurement devices; exercise equipment, e.g., tread mills; body weight sensors; motion sensors; position sensors, e.g., bed sensors; chair sensors; portals in doorways; refrigerator and food devices; bathroom facilities devices; and the like. The intelligent devices/appliances include consumer and home devices and appliances that are capable of receipt of data and data processing, such as transmitting, displaying, and/or storing data. Moreover, the intelligent devices/appliances may include functionality such as sensing or monitoring various physiologic parameters, e.g., weight, heart rate, etc. Examples of intelligent devices/appliances include devices and appliances having refrigerators, weight scales, toilets, televisions, doorframe activity monitors, bedside monitors, and bed scales.

In some implementations, the hub 140 is configured to ensure privacy requirements via predetermined methods, e.g., a source of therapeutic and wellness data 135 representing an individual's ingestion of medication is considered sensitive data requiring some form of data protection. Although the signals associated with the sensitive therapeutic and wellness data 135 may remain undetectable beyond the individual's body, once received by the receiver 1358 or hub 140, the therapeutic and wellness data 135 may be cleansed or encrypted before being forwarded within system 100.

Furthermore, the hub 140 may be configured to include combinations of devices. One such combination is a receiver configured as a patch in communication with a hub 140, implemented as a handheld device or a mobile telephone. For example, the patch receiver wirelessly transmits therapeutic and wellness data 135 to the mobile telephone having a receiver and a software agent. The receiver of the mobile telephone receives the IEM data. The software agent processes the therapeutic and wellness data 135 and presents information related to the therapeutic and wellness data 135 via, for example, a graphical user interface (GUI). In some aspects, the software agent generates displays with a predetermined "look and feel," i.e., recognizable to a user as belonging to a predetermined group of software programs, GUIs, source devices, communities, etc. To illustrate further, the therapeutic and wellness data 135 may include data about an ingested medication. Once the therapeutic and wellness data 135 are received by the mobile phone, which in this example is configured to function as a receiver, a hub, and an IEM data system, the software agent may compare the data about the medication to a predetermined medication regimen. Upon verification that the proper medication has been ingested at the proper time, the software agent disables an audible alarm scheduled to alert the individual to take the (already ingested) medication, thus averting an unnecessary reminder. The software agent, via the GUI, displays a standard message to the individual notifying of the medication ingested and the time of the next dosage.

Moreover, the software agent may include functionality to generate or facilitate a financial transaction. In one example, upon occurrence of a certain event, such as verification that the proper medication has been ingested at the proper time, the software agent generates a predetermined charge for the ingested medication, the verification service, or both. The charge is transmitted to a financial system. For example, the patient's mobile phone transmits the charge via an IEM data system to a commercial system associated with the patient's financial institution, where the charge is automatically applied against a financial account of the patient. The software agent may also contact other commercial systems 165 to order additional medication, consult with a physician, consult with a pharmacist, and the like.

System 100 may also include one or more IEM data systems 150. The IEM data system 150 may be implemented as a computer configured to receive therapeutic and wellness data 135 from the hub 140 and present the therapeutic and wellness data 135 in conjunction with other information. IEM data systems 150 may, for example, collect, manipulate, calculate, transmit, receive, store, and/or communicate at least a portion of the therapeutic and wellness data 135. Each of the IEM data systems 150 may be configured around predefined function(s) or service(s) provided via system 100, and may be integrated, interoperate, intercommunicate, otherwise share, or further the collection, management, distribution/dissemination, billing, and/or other activities related to the therapeutic and wellness data 135. Furthermore, one or more IEM data systems 150 may be associated with one or more commercial systems 165, and may share the therapeutic and wellness data 135 with the commercial systems 165.

The IEM data systems 150 may include one or more of the following: a therapy controller; a response determinator; a feedback loop systems for providing feedback to a user regarding whether medication integrated with an IEM 110 has been taken properly; decision support systems; auto prescription refill systems; patient tools including web sites, databases, tracking tools to assist a patient in health management and well being; behavioral medicine systems to monitor behavioral data using questionnaires, profile assessments, and the like; incentive systems to provide incentives, rebates, and coupons to a patient; personalized commercial products and services, such as integrating a receiver into an earring or adorning the receiver with a cartoon character; auto billing systems for billing a patient or a corresponding insurance company based on therapeutic and wellness data representing usage of the system 100 or representing medicine associated with IEM 110; tracking systems to track the medicine associated with the IEM 110 from manufacture to consumption; interdiction systems to aid law enforcement in searching, seizing, and/or tracking the medicine associated with the IEM 110; subscription systems to provide integrated information feeds from one or more sources of information, such as web sites, personalized medical information, medical alert services, music, community information, and the like; data collections and storage systems for the therapeutic and wellness data; approval systems to enable a physician and/or a pharmacist to approve a refill request, a dosage of medicine associated with the IEM, and the like; forecasting systems for aggregating data and/or facilitating analysis of the aggregated data to generate predictive information; financial systems to support financial transactions associated with the system 100; an IEM data phone system configured to execute applications, such as pill regimen scheduling, alerts, reminders, patient tools, social networking, billing, subscription services, approvals, and financial transactions.

Commercial systems 165 may include one or more systems, such as a financial system, a pharmacy system, a healthcare system, an insurance system, an employer system, a government system, and any other system(s) that an IEM data system 150 may access, provide, share, and/or retrieve information in connection with processing the therapeutic and wellness data 135.

Figure 2:
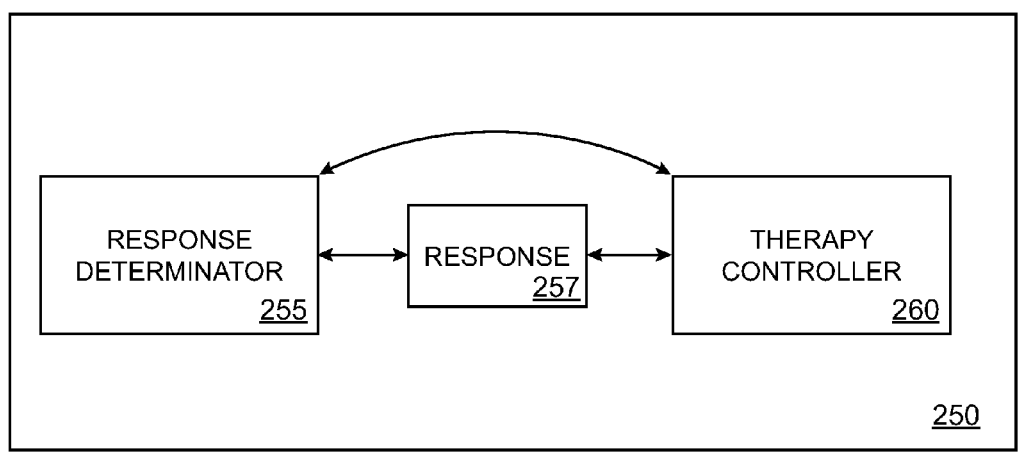
FIG. 2 depicts an IEM data system including a therapy controller and a response determinator.

FIG. 2 depicts an example of an IEM data system 250, including a response determinator 255, a response 257, and a therapy controller 260. The IEM data system 250 and, in particular, the response determinator 255 determines a response to a dosage of a substance using the therapeutic and wellness data 135. The therapy controller 260 uses the determined response to control the administration of the substance.

In some implementations, the therapeutic and wellness data 135 received from IEM 110 and/or wellness devices 112 includes an indication of a dosing event, such as an ingestion time, an identification of the ingested substance, a dose, i.e., an amount of the ingested substance, and the like. Moreover, the therapeutic and wellness data 135 may be processed to develop a profile representing how a given drug affects (e.g., in terms of pharmacokinetic and/or pharmacodynamic models) a patient. In some implementations, the response determinator 255 determines this profile as the response 257 described further below.

Once the response 257 is determined, therapy controller 260 uses the determined response 257 to forecast the impact of the substance, e.g., the medication, on the patient. The response 257 may represent the effect of a dose on a patient and may be used to forecast the effect of given subsequent doses. For example, the response 257 may model the effect of serum levels based on a single dose of a medicine integrated with the IEM 110. The therapy controller 260 may include a control-loop, described further below with respect to FIG. 7, to control, based on response 257, the administration of the medicine integrated with the IEM 110. For example, one might find, as determined from therapeutic and wellness data 135, that a patient is not doing so well at a given time. One might look back at the response 257 and determine that the levels of the medicine in the blood are getting low when the patient is sensed as not doing well. The therapy controller 260 may use the response 257 to make a determination to vary, e.g., increase, decrease, or maintain, the dosing frequency or vary the dose, e.g., the amount. In short, the IEM 110 and the therapeutic and wellness data 135 (which is includes IEM data) provides a way to develop the response 257 and then control the administration of the medicine.

Figure 3A:
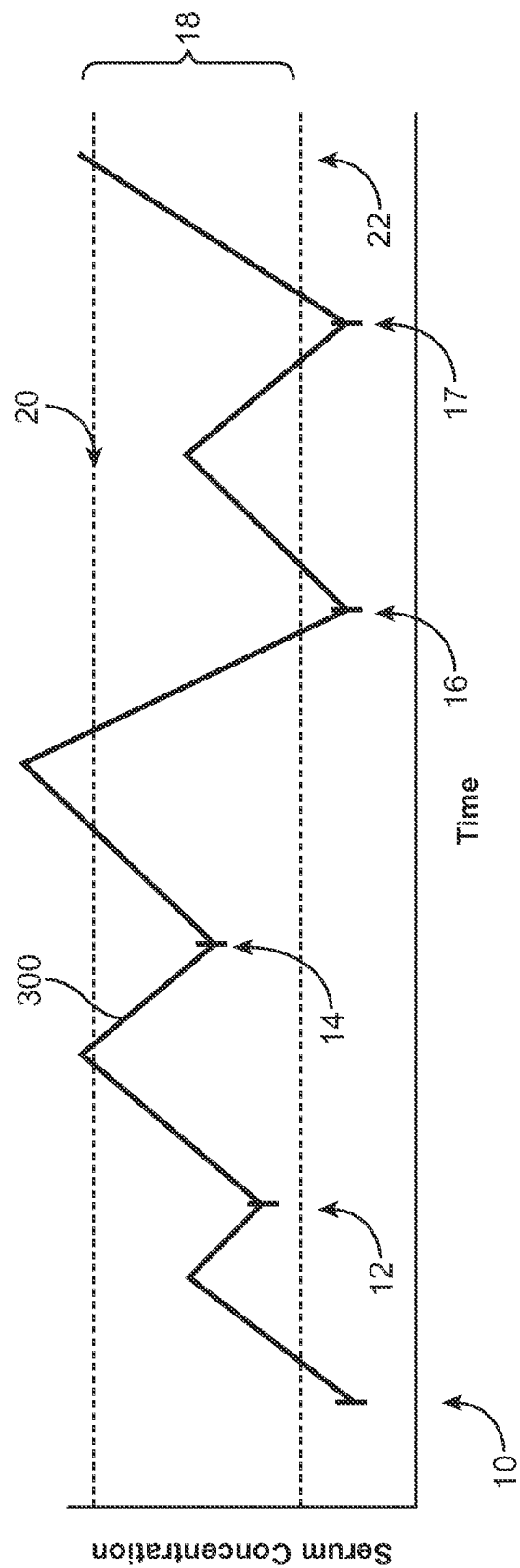
FIGS. 3A-B depict plots of serum concentration over time.

FIG. 3A depicts an example plot 300, in which the patient takes doses of medication at times 10, 12, 14, 16, and 17. The medication is integrated with the IEM 110, and the IEM data (which is included in the therapeutic and wellness data 135) includes dose event information including the times 10-17 the doses were taken. The dose times 10-17 were taken at uneven time intervals. Moreover, the plot 300 depicts that the therapeutic range 18 is bound by a toxic limit 20 and a lower limit 22. The serum concentration in this plot rises above toxic limit 20 and drops below the lower limit 22 due to the uneven dosing times. The data of plot 300 may be used as therapeutic and wellness data 135.

Figure 3B:
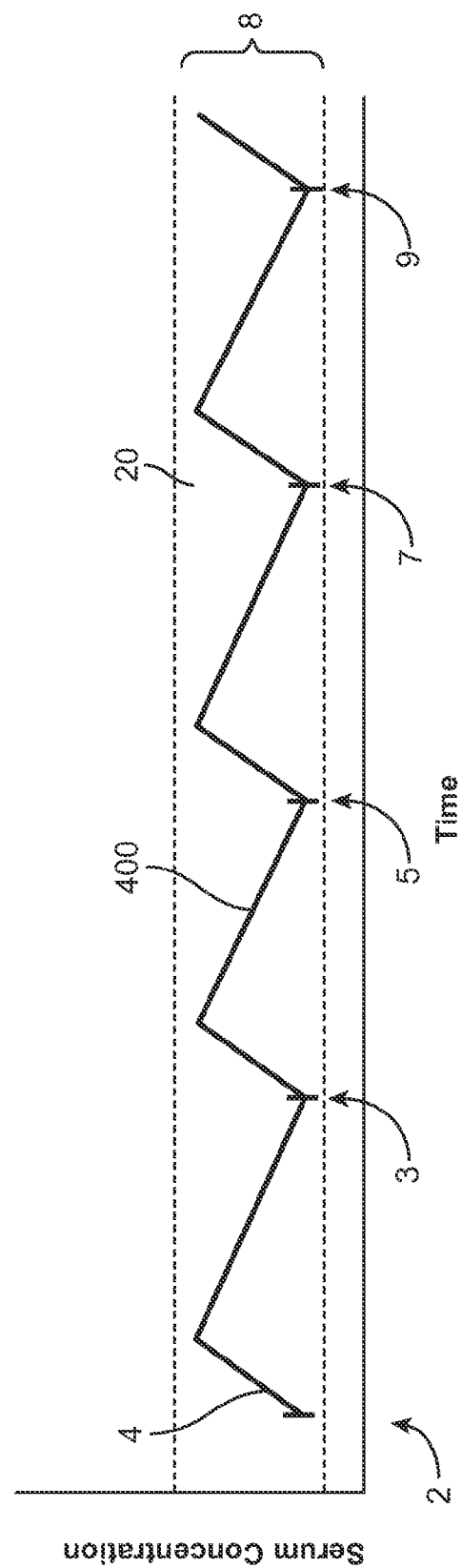

The response determinator 255 may use the therapeutic and wellness data 135 (including IEM data) to determine the response 257. The IEM data system 250 may then use the determined response to control therapy. Specifically, the therapy controller 260 may control when and how much of a dosage a patient should take given the response 257. For example, at point 14, the IEM data system 250 may use the response 257 to determine that at point 14 a dose should not be taken at time 14 or, if a dose is taken, that the dose be reduced to avoid the toxic limit 20. In this example, the IEM data system 250 may control the administration by, for example, sending an alert to the patient indicating an amount and/or a time medication should be ingested. Moreover, IEM data system 250 may control the "optimum" times a patient should take a given dose, and then monitor the actual consumption via the therapeutic and wellness data 135. In contrast to FIG. 3A, FIG. 3B depicts a plot 400 in which the patient takes doses of regular medication at times 2, 3, 5, 7, and 9, and the serum blood levels are controlled by therapy controller 260 to stay within an acceptable range 8, i.e., below the toxic limit 20 and above the lower limit 22.

The therapeutic and wellness data 135 may include event data representing the time a dose of a substance integrated with an IEM 110 was taken. Moreover, the therapeutic and wellness data 135 may include different types of data including one or more of the following: ingestion event information, such as ingestion time, identification of the ingested substance, expiration date of the substance, and dosage amount; physiological parameters associated with a response to a dose; dosage of an intravenous substance; heart rate; blood pressure measurements; optical measurements of blood; body temperature; weight; subjective measures of wellness as reported by a patient or a healthcare provider; and the like.

Figure 4:
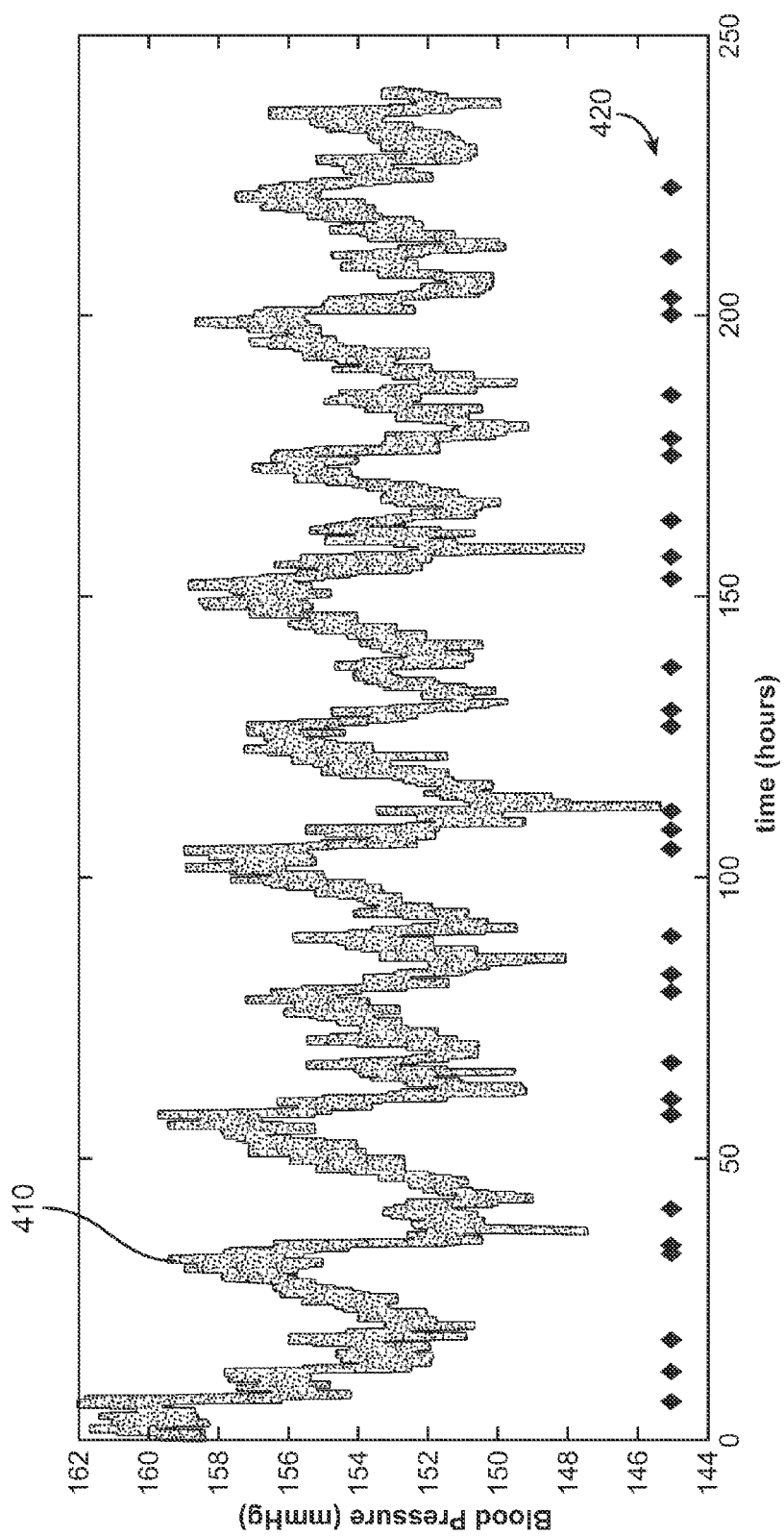
FIG. 4 depicts a plot of blood pressure over time, when a patient is given medication integrated with the IEM.

FIG. 4 shows an example of therapeutic and wellness data 135 in the form of blood pressure measurements 410 and dosing events 420 over time in hours. The dose events 420 are determined from the consumption of the IEM 110, and the dose events 420 may be correlated with the blood pressure data 410. The response determinator 255 uses the dose events 410 and blood pressure measurements to determine the response 257, although the response determinator 255 may use other types of data to determine the response 257. The response 257 thus represents how a system, e.g., an organism, a patient, etc., reacts to the dose integrated with the IEM 110.

The response 257 may be determined in a variety of ways. However, in some implementations, the response 257 is determined as follows:

$$Y=AH \qquad \text{Equation 1,}$$

wherein matrix A and matrix H are multiplied to yield matrix Y, wherein the matrix Y represents a matrix of observations, the matrix A represents the dose events, and the matrix H represents the response 257, e.g., the reaction of a patient given a dose of the substance, such as a drug.

The matrix of observations Y represents therapeutic and wellness data 135. For example, the matrix of observations Y may correspond to an n by 1 matrix, wherein n corresponds the number of measurements, e.g., observations, samples, etc. To illustrate, if the serum concentration observations 300 of FIG. 3A includes 300 measurements, n is equal to the 300 sample measurements. In this example, the Y matrix is 300 by 1 matrix. Although the previous example used serum concentration as the observations, any other type of therapeutic and wellness data 135 may be used as well. For example, the matrix of observations Y may include other types of therapeutic and wellness data 135, such as the blood pressure measurements at times 2-9 of FIG. 3B, and the like.

The dose events A represent the times when the IEM 110 signaled that a dose was taken. For example, the dose events A may include dosage times 10-17, dosage times 420 at FIG. 4, and the like. Moreover, the dose events may be represented as real time values when the doses are taken or as binary values. For example, the real times may be represented as actual time values, e.g., 12:01:00 PM, and the binary values may be represented as 0, 0, 0, and 1, wherein the zeroes represent that no dosing events were detected at the first three time intervals, but the last interval includes a dosing event. In some implementations, the dose events matrix A may be implemented as an n by m matrix, wherein m represents the quantity of dosage times. Referring to FIG. 4, there are 28 times, which are represented by the diamonds at 420, so m is equal to 28.

The response matrix H may model the reaction of a patient given a dose of the substance, such as a drug. The reaction may be measured by sensors, such as the IEM 110 or the wellness devices 112. In some implementations, the response matrix H is implemented as an m by 1 matrix.

Although the matrices A, H, and Y are each described in terms of a matrix, matrices A, H, and Y may also be implemented in other ways, such as a vector, a data structure, and the like.

The response matrix H may be determined in a variety of ways, but in some implementations, the response matrix H may be determined using the following equation:

$$H=(A^TA)^{-1}A^TY \qquad \text{Equation 2,}$$

wherein the $A^T$ represents the transpose of matrix A, $(A^TA)^{-1}$ represents the inverse of the result of a matrix multiplication of matrix A and matrix $A^T$. The resulting response matrix H may be used as the response, e.g., of a patient, over time given a single dose. Although the above solves for the response using matrix H, the response matrix H may be solved using other approaches, including, for example, a general linear model.

Figure 5:
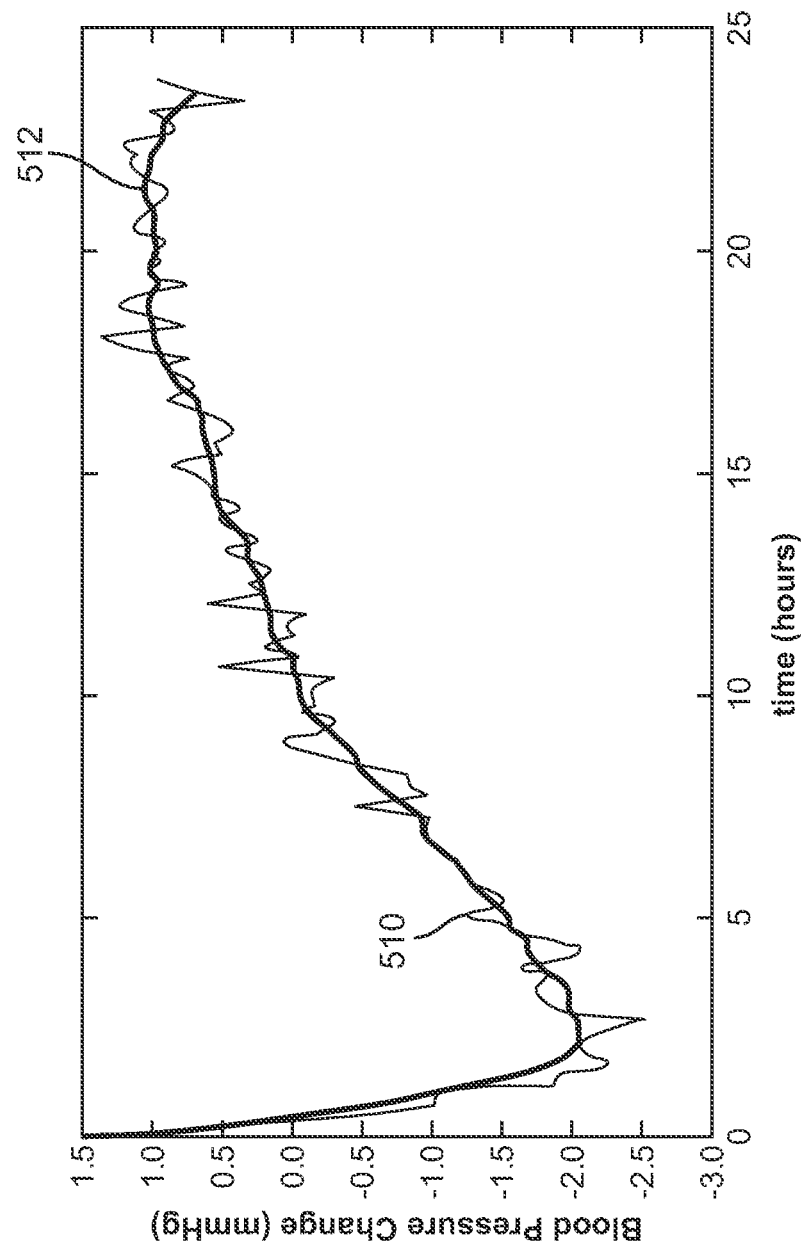
FIG. 5 depicts a plot of a response.

FIG. 5 depicts an example of the response 257, which is plotted at 510 with a smoothed estimate 512 of the plotted response 510. The response 257 plotted at 510 corresponds to the response matrix H determined using, for example, Equation 2 above. The response 257 plotted at 510 is depicted for a single dose given a single type of therapeutic and wellness data 135, e.g., blood pressure change data given a single dose taken at time zero (0). Although FIG. 5 depicts a response determined using blood pressure data, other types of therapeutic and wellness data 135 and corresponding responses may be determined using the response matrix H.

Although the above example represents a single dose, the response matrix H may be determined for multiple doses. When that is the case, the following equation may be used:

$$Y=A_1H_1+A_2H_2 \qquad \text{Equation 3,}$$

wherein the matrix $A_1$ represents dose events associated with a dose, matrix $H_1$ represents the response for matrix $A_1$, matrix $A_2$ represents dose events associated with another dose, matrix $H_2$ represent the dose response for matrix $A_2$, and matrix Y represents the observations included in the therapeutic and wellness data 135. Moreover, the response matrixes $H_1$ and $H_2$ may be solved in a variety of ways. For example, the combined matrixes $H_1$ and $H_2$ may be solved based on the following equation:

$$Y = [A_1 A_2] * \begin{bmatrix} H_1 \\ H_2 \end{bmatrix}. \qquad \text{Equation 4}$$

In some implementations, a plurality of types of therapeutic and wellness data 135 may be used. These different types of data may be provided by IEM 110 and/or wellness devices 112 and included in the therapeutic and wellness data 135. Moreover, the different types of data may be used to determine a response matrix H, either as a separate matrix or a combined matrix. The following equations may be used in connection with different types of data:

$$Y_1=A_1H_1$$

$$Y_2=A_3H_2 \qquad \text{Equations 5-6,}$$

wherein matrix $Y_1$ may correspond to a first type of data, and $Y_2$ may correspond to another type of data. For example, $Y_1$ may correspond to the weight of the patient over time, and $Y_2$ may correspond to blood glucose measurements over time received from one of the wellness devices 112. The data $Y_1$ and $Y_2$ may be included in the therapeutic and wellness data 135. In this example, the response determinator 255 may calculate the responses matrices $H_1$ and $H_2$, separately or in combination.

Figure 6:
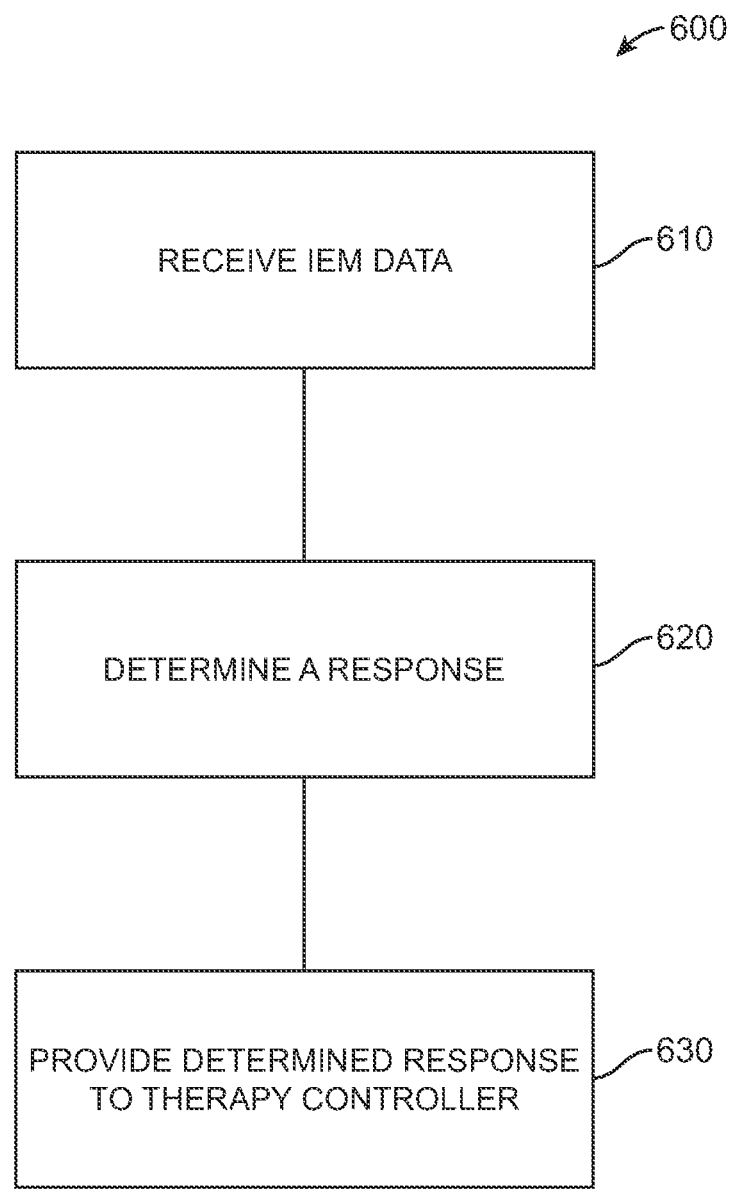
FIG. 6 depicts a process for determining a response based on IEM data.

FIG. 6 depicts a process 600 for determining a response.

At 610, IEM data may be received. For example, response determinator 255 may receive therapeutic and wellness data 135 from the hub 140. The therapeutic and wellness data 135 may include one or more of the following types of data: ingestion event information, such as ingestion time, identification of the ingested substance, expiration data of the substance, and dosage amount; physiological parameters associated with a response to a dose; dosage of an intravenous substance; heart rate; blood pressure measurements; optical measurements of blood; body temperature; weight; subjective measures of wellness as reported by a patient or a healthcare provider; measuring or tallying doses of an inhalant; an inhalation time; an identity of an inhaled substance; EKG data; activity management data; galvanic skin response data; respiratory data; fluid status data; heart rate variability; a time of insertion; a time of drinking; and the like.

At 620, a response may be determined. For example, the response determinator 255 may determine the response 257 to one or more doses of medicine integrated with the IEM 110. The response determinator 255 may use one or more types of therapeutic and wellness data 135 and one or more of Equations 1-6 to determine the response 257 as the response matrix H. Although the response may be determined using Equations 1-6, other numerical techniques may be used as well to determine the response 257. For example, the response may be determined using one or more of the following techniques: least-squares approximation, maximum-likelihood methods, Bayesian estimation, Weiner filtering, Kalman filtering, Maximum a posteriori (MAP) estimator, neural networks, and function optimization techniques.

Moreover, in some implementations, the type of therapeutic and wellness data 135 corresponds to the type of response 257. For example, if blood pressure medication is integrated with the IEM 110, the type of therapeutic and wellness data 135 used to determine the response 257 corresponds to measurements indicative of blood pressure, such as blood pressure measurements received from one of the wellness devices 112 as well as dose event data from the IEM 110. However, in some implementations, the type of therapeutic and wellness data 135 used to determine the response 257 may not be directly linked to the type of response. For example, returning to the previous blood pressure example, the therapeutic and wellness data 135 may further include body temperature measurements, weight, heart rate, data from smart appliances, and subjective data reported by the patient providing an indication of perceived wellness.

At 630, the response determinator 255 provides the determined response 257 to therapy controller 260. The response 257 provided at 630 may be modified to represent a population or a subset of the population rather than a single patient. The term population refers to all users of the substance being administered at system 100, and the term subset of the population refers to a group of the population, such as a subset chosen based on a trait or a demographic, e.g., all females. For example, the responses of a plurality of patients may be combined to determine the response 257 representative of a population or a subset of the population. In some implementations, rather using the response provided at 630, the response 257 is obtained from other sources. For example, the response 257 may be provided by mechanisms, such as a web site, another system, medical journals, pharmacodynamic studies, pharmacokinetic studies, and the like.

The determined dose response 257 may be used by therapy controller 260 to control therapy of a patient by controlling the dose or when the dose is administered. For example, the response 257, e.g., a dose response, provided at 630 may be used by therapy controller 260 to optimize therapy using a closed-loop control system. Although the therapy controller 260 is described with respect to a closed-loop control system, other control mechanisms may be used as well. For example, instead of a closed-loop control system, one or more of the following may be used: a model-based controller, an optimization controller, a state variable controller, a neural network, a non-linear controller, a linear controller, an adaptive controller, Kalman filtering, a Bayesian controller, a fuzzy logic controller, a machine learning controller, a genetic algorithm controller, a stochastic controller, an intelligent controller, and the like.

Figure 7:
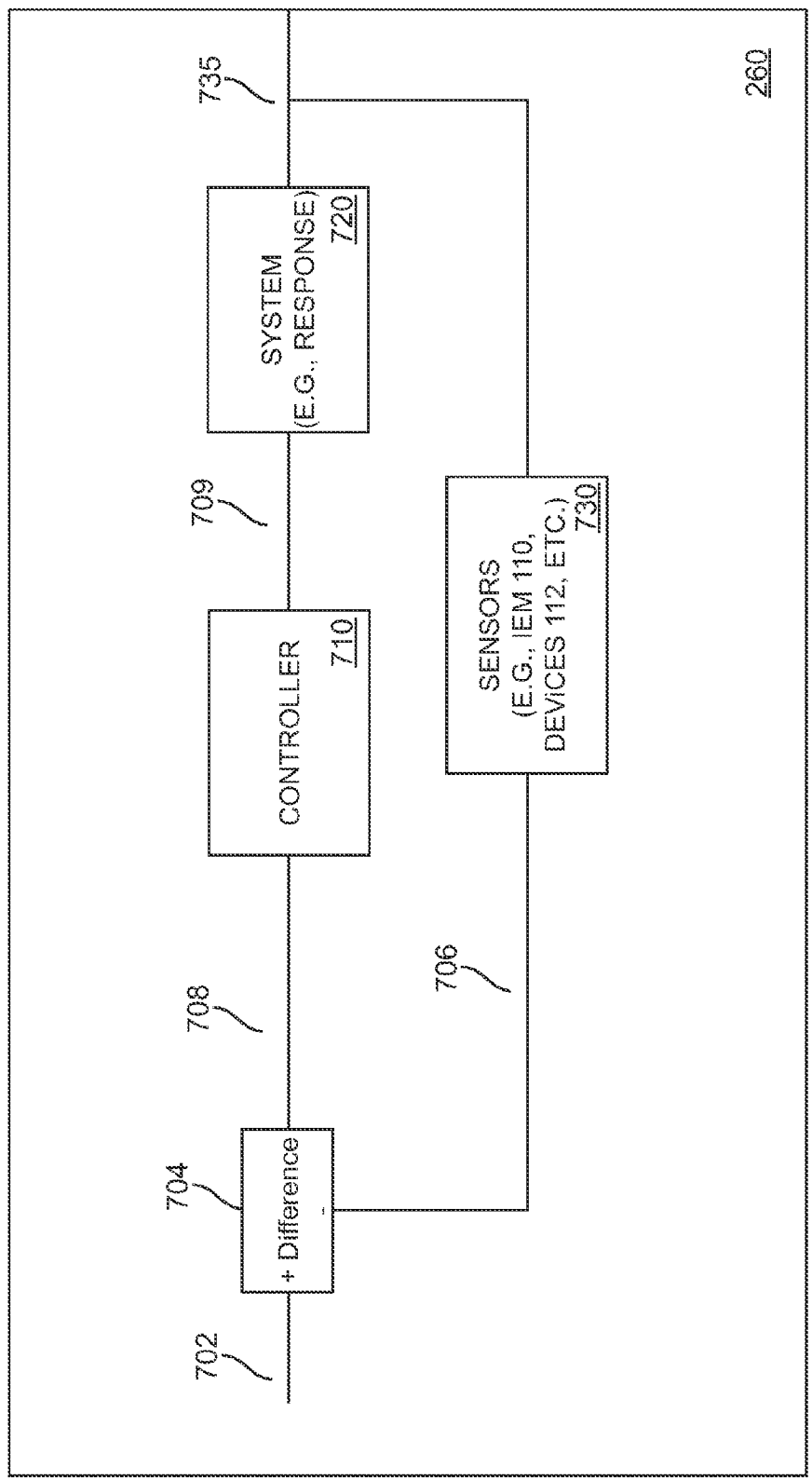
FIG. 7 depicts a therapy controller.

FIG. 7 depicts an example of therapy controller 260 implemented as a closed-loop control system. The therapy controller 260 may include a controller 710, a system 720 representing a response, and one or more sensors 730.

The therapy controller 260 may be used to control the administration of one or more doses of a substance to achieve a desired output. Generally, the controller 710 receives a measured error 708, generates the input 709 to the system 720, and repeatedly generates the input 709 to achieve a desired output 735 at system 720. The measured error 708 represents feedback to the controller 710. Because system 720 represents a response, e.g., a dose response of a patient, the controller 710 is, in effect, varying the dose, e.g., the dose, e.g., amount, of the substance integrated with the IEM 110, and/or varying the time the dose is administered.

To illustrate with an example, given a measured output 708 of 109.0 mmHG, e.g. from a blood pressure measurement device, the set point 702 for this type of measurement may be 110.5 mmHG. The set point 702 may be a predetermined value and, in some cases, may be equal to a reference value, such as a desired blood pressure for a patient. Next, controller 710 receives the measured error 708 of 1.5 mmHG, i.e., the difference 704 between 110.5 and 109.5. The measured error 708 of 1.5 mmHG is then used by the controller 710 to generate the input 709 to the system 720. The input 709 causes system 720 to generate the desired output 735, such as the dose of the substance integrated with the IEM 110, and/or varying the time the dose of the substance is administered.

Referring again to FIG. 5, when the system 720 corresponds to, for example, response 510, system 720 provides the desired output 735 indicative of another dosage of medication as FIG. 5 represents that a dose increases blood pressure by 1.5 mmHG. This indication may be provided as an alert to be sent to the patient and/or may control a sensor to administer the substance. For example, the desired output 735 may cause an alert to the patient to ingest another dose of the medication integrated with an IEM or vary the dosage amount, the effects of which are monitored by sensors 730. In this example, the additional ingested dose of the substance, e.g., medication, may control therapy by increasing the patient's blood pressure to the desired 110.5 mmHG. One or more of the sensors 730 may provide the measured output 706 of 110.5 mmHG. The value of 110.5 mmHG is feedback provided to the difference component 704, at which point the above-described feedback process repeats generating another output 735, and so forth as described above.

The therapy controller 260 thus repeatedly controls the dose and/or the time the dose is administered, e.g., the sensors 730 repeatedly provide the measured output 706, the controller 710 repeatedly receives measured error 708 and repeatedly provides input 709 to system 720, and so forth. Returning to the previous example, as long as the measured error 708 remains zero (0), the controller 710 may generate the input 709, such that the output 735 does not correspond to another dose of the substance integrated with the IEM since the measured error indicates that the measured blood pressure of 110.5 equals the desired blood pressure of 110.5. However, when the blood pressure rises or falls, this change is detected by sensors 730, and sent as feedback, e.g., measured output 706, repeating the above described control-loop process to vary the administration of the substance, e.g., medication, integrated with the IEM.

Although the previous example is described with respect to blood pressure measurements, any other type of data, e.g., therapeutic and wellness data, may be provided by sensors 730 and used as feedback to controller 710. Moreover, although the previous example is described with respect to the response depicted at FIG. 5, other responses may be used as well.

The sensors 730 may include one or more IEMs 110 and one or more wellness devices 112. Moreover, the sensors 730 may provide the therapeutic and wellness data 135 or any data indicative of aspects of a patient being administered a therapy with the IEM 110.

The system 720 represents the response of the system being controlled. For example, the system 720 may be implemented as the response 257 provided at 630, although responses from other sources may be used as well. Moreover, the response 257 used by system 720 may represent an individual, a population, such as all patients ingesting the medication, or a subset of the population, such as a specific demographic or trait. In any case, the system 720 generally represents the patient using the substance integrated with the IEM 110.

Moreover, in some implementations, the difference component 704 is implemented as a difference amplifier, although digital implementations may be used as well. The controller 710 may be implemented as a filter, a phase-locked loop, although digital implementations may be used as well.

Figure 8:
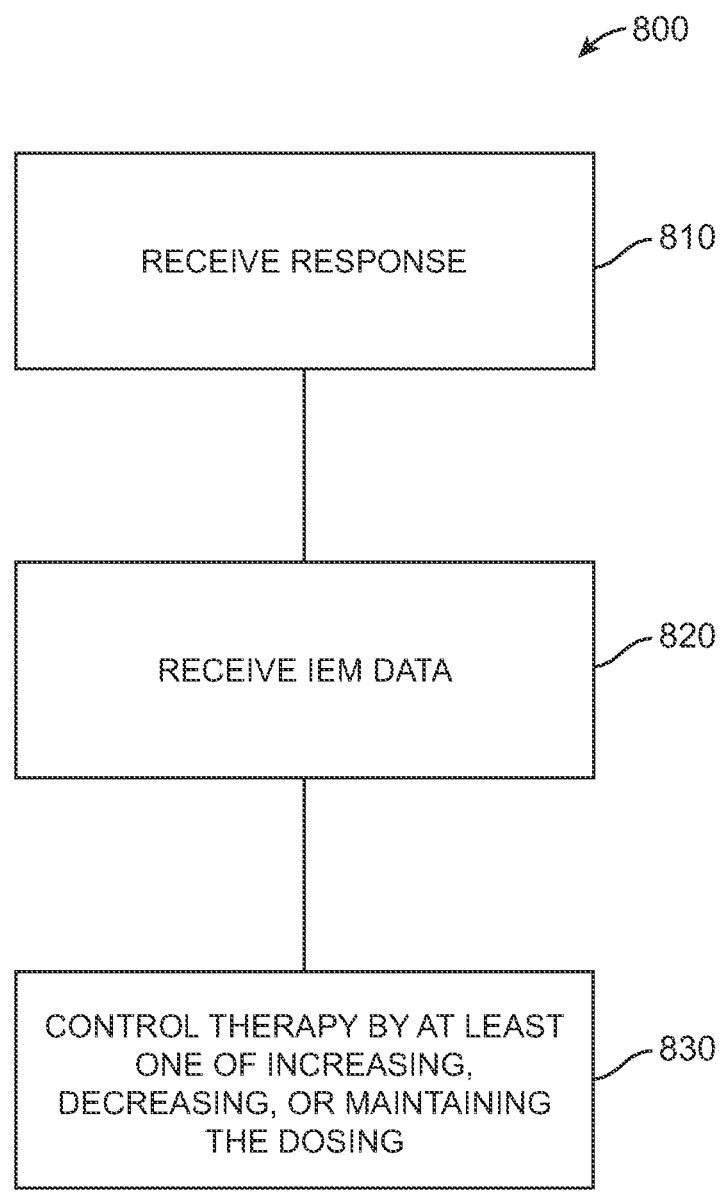
FIG. 8 depicts a process for controlling therapy.

FIG. 8 depicts a process 800 for controlling therapy using therapy controller 260.

At 810, a dose response is received. For example, therapy controller 260 may receive the response 257 provided at 630. The response 257 may be used as the system 720. Alternatively, the response used by system 720 may be obtained from other sources, such as a web site, another system, medical journals, pharmacodynamic studies, pharmacokinetic studies, and the like. Moreover, the system 720 may include a plurality of responses to provide comprehensive control of the overall wellness of the patient ingesting the IEMs 110 and integrated substance.

At 820, IEM data may be received. For example, IEM 110 and/or wellness devices 112 may provide therapeutic and wellness data 135. In this regard, the IEM 110 and/or wellness devices 112 operate as sensors 730, providing the measured output 706 in the form of therapeutic and wellness data 135. The measured output is processed further to obtain the measured error 708, which is provided to controller 710.

At 830, controller 710 controls therapy, e.g., the administration of a drug, by providing the input 709 to system 720. The controller 710 may vary, i.e., increase, decrease, or maintain, its output, which serves as the input 709. Moreover, this variation is determined based on the measured error 708. For example, in some implementations, the controller 710 repeatedly varies input 709 until the measured output 706 is about equal to the set point 702, which represents a predetermined, reference value. The system 720 thus generates the output 735 in response to the input 709. Moreover, the output 735 may be provided to one or more of the sensors 730 and/or may be provided as an alert to a patient using the IEM 110 and integrated substance. For example, the output 735 may be sent to a wellness device that controls a dose administered to a patient or controls the time, and thus frequency, of administration of the dose. Moreover, the alert may be provided to the commercial system(s) 165 to provide information to, for example, a physician, a pharmacist, etc.

In some implementations, the subject matter described herein may provide one or more of the following advantages. For example, the use of IEM 110 and therapeutic and wellness data 135 may provide direct measurement of dosing events rather than data that is self-reported by a patient, and thus more likely to be in error. Moreover, the receivers 130A-B may be implemented to monitor continuously for various types of IEM data. This continuous data monitoring may provide a more complete picture of the well-being of the patient, when compared to monitoring only a single aspect of the patient. Moreover, the continuous monitoring by receivers 130 may allow data aggregation. Data aggregation allows data to be correlated and then mined to identify symptoms not readily identified with only a single type of data. Moreover, data mining may be used to identify data anomalies or patterns, which can be incorporated into treating the patient using therapy controller 260. For example, data mining may be used to uncover relationships related to patient demographics, co-pharmacy, nutrition, etc. In short, the data aggregation may provide a more complete picture of the therapy being provided to the patient and the corresponding well-being of that patient, when compared to only a single type, or mode, of data obtained from a sensor.

Moreover, in some implementations, the subject matter described herein may be used to control behavior. Referring to FIG. 1, the matrix of observations Y may include values representative of a patient's adherence to a therapy (e.g., a time value when a patient takes a medication, an error value representing a time difference between when the patient takes medication and when the patient is supposed to (per a therapy regime) take the medication, and so forth), and the matrix A represents an indication of an intervention (e.g., a call or an email from a nurse to remind the patient to take the medication, and the like) or an incentive (e.g., a discount on the medication, a discount on an insurance policy, and the like). In this example, the matrix H represents the response 257 of the patient to the incentive or intervention. As such, the response 257 may be used to control the incentives and/or interventions in order to obtain a desired response in a given patient (which may be unique to that patient).

The subject matter described herein may be embodied in systems, apparatus, methods, and/or articles depending on the desired configuration. In particular, various implementations of the subject matter described may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. For example, the components of, e.g., wellness devices 112, IEM 110, receivers 130A-B, hub 140, IEM data systems 150 and 250, response determinator 255, therapy controller 260, and/or aspects of processes 600 and 800 may be realized in digital electronic circuitry, integrated circuitry, specially designed ASICs (application specific integrated circuits), computer hardware, firmware, software (including computer programs), and/or combinations thereof.

These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor. Similarly, systems are also described herein that may include a processor and a memory coupled to the processor. The memory may include one or more programs that cause the processor to perform one or more of the operations described herein.

Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. The foregoing description is intended to illustrate but not to limit the scope of the invention, which is defined by the scope of the appended claims. Other embodiments are within the scope of the following claims.

What is claimed:

1. A system comprising:
   a processor; and
   at least one memory, the processor and the at least one memory configured to provide a response determinator to:
   receive therapeutic and wellness data;
   determine, based on the received therapeutic and wellness data, a response representing a reaction to a substance integrated with an ingestible event marker; and provide the determined response; and
   wherein the response determinator determines the response as a response matrix, H, according to the following equation:

$$H = (A^T A)^{-1} A^T Y,$$

wherein A represents one or more times that a dose of the substance is ingested, $A^T$ represents a transpose of matrix A, $(A^T A)^{-1}$ represents an inverse of a matrix multiplication of matrix A and matrix $A^T$, and Y represents a matrix of observations including the therapeutic and wellness data.

2. The system of claim 1, wherein the therapeutic and wellness data includes ingestible event marker data received from the ingestible event marker integrated with the substance, the ingestible event marker providing a signal when the substance is ingested.

3. The system of claim 1, wherein the therapeutic and wellness data includes data representative of physiological aspects associated with the ingestion of the ingestible event marker and the substance.

4. The system of claim 1, wherein the therapeutic and wellness data includes one or more of the following: an ingestion time; an identification of the substance; an expiration date of the substance; a dosage amount for the substance; one or more physiological parameters associated with the reaction to at least one dose of the substance; a dosage of an intravenous substance; a heart rate; a blood pressure measurement; an optical measurement; a body temperature; a weight; an amount of an inhalant; an inhalation time; an identity of an inhaled substance; a galvanic skin response; an insertion time; and a drinking time.

5. The system of claim 1, wherein the response determinator determines the response as a function of the therapeutic and wellness data.

6. The system of claim 1 further comprising:
   a therapy controller configured to control, based on the response, at least one of an amount the substance and a time of the substance is ingested.

7. A system comprising:
   a processor; and
   at least one memory, the processor and the at least one memory configured to provide a therapy controller to:
   receive a response representing a reaction to a substance integrated with an ingestible event marker;
   receive therapeutic and wellness data; and
   control, based on the received response and the received therapeutic and wellness data, at least one of a dose of the substance and a time of the dose of the substance;
   wherein the response is determined as a response matrix, H, according to the following equation:

$$H = (A^T A)^{-1} A^T Y,$$

wherein A represents one or more times that a dose of the substance is ingested, $A^T$ represents a transpose of matrix A, $(A^T A)^{-1}$ represents an inverse of a matrix multiplication of matrix A and matrix $A^T$, and Y represents a matrix of observations including the therapeutic and wellness data.

8. The system of claim 7, wherein the therapy controller uses a closed-loop to control at least one of the dose of the substance and the time of the dose of the substance.

9. The system of claim 7, wherein the therapy controller uses a closed-loop to vary an input to the response to generate an output of the response, the output corresponding to at least one of the dose of the substance and the time of the dose of the substance.

10. The system of claim 7, wherein the ingestible event marker data are received from the ingestible event marker integrated with the substance, the ingestible event marker providing a signal when the substance is ingested.

11. The system of claim 7, wherein the therapeutic and wellness data represents physiological aspects associated with the ingestion of the ingestible event marker and the substance.

12. The system of claim 7, wherein the response is determined based on the reaction of at least one of an individual patient, a population, and a subset of the population.

13. The system of claim 7, wherein the response is determined as a function of the therapeutic and wellness data.

* * * * *